(12) United States Patent
Vijaybhaskar et al.

(10) Patent No.: US 7,173,166 B2
(45) Date of Patent: Feb. 6, 2007

(54) DNA SEQUENCE FOR ROOT PREFERRED GENE EXPRESSION IN PLANTS

(75) Inventors: Virupapuram Vijaybhaskar, Andhra Pradesh (IN); Imran Siddiqi, Andhra Pradesh (IN)

(73) Assignee: Council of Scientific and Industrial Reseach, New Delhi (IN)

( * ) Notice: Subject to any disclaimer, the term of this patent is extended or adjusted under 35 U.S.C. 154(b) by 0 days.

(21) Appl. No.: 10/847,539

(22) Filed: May 17, 2004

(65) Prior Publication Data

US 2005/0257286 A1    Nov. 17, 2005

(51) Int. Cl.
  *A01H 5/00*    (2006.01)
  *C12N 15/82*    (2006.01)
(52) U.S. Cl. .................. 800/287; 800/298; 435/419; 536/24.1
(58) Field of Classification Search ................ 800/278, 800/287, 298; 536/24.1; 435/320.1, 419
  See application file for complete search history.

(56) References Cited

OTHER PUBLICATIONS

Ulmasov et al., Composite Structure of Auxin Response Elements, The Plant Cell 7:1611-1623, 1995.*
Donald et al., Mutation of either G box or I box sequences profoundly affects expression from the Arabidopsis rbcS-1A promoter, the EMBO Journal 9: 1717-1726, 1990.*
Muhitch et al., Isolation of a promoter sequence from the glutamine synthetase1-2 gene capable of conferring tissue-specific gene expression in transgenic maize, Plant Science, 163:865-872, 2002.*
Ito et al., Xylem-specific expression of wound-inducible rice peroxidase genes in transgenic plants, Plant Science 155:85-100, 2000.*

\* cited by examiner

*Primary Examiner*—Elizabeth F. McElwain
(74) *Attorney, Agent, or Firm*—Frommer Lawrence & Haug LLP; Thomas J. Kowalski; Anne-Marie C. Yvon (57) ABSTRACT

Expression of DNA sequences in a preferred manner in the roots of a plant is often desirable. For instance improved resistance to soil-borne pathogens may be attained by expression of a pathogen resistance gene in a part of the plant such as the root that may be the site of infection. It is therefore desirable to develop tissue-preferred promoters that are capable of directing the expression in a preferred manner in plant roots, of another DNA sequence that is operably linked to the promoter sequence. Further, it is desirable to have access to multiple promoters with similar expression patterns since these may differ with respect to their degree of successful applicability in different plant species where such expression may be desired. Here we describe the isolation and analysis of a DNA sequence from the upstream regulatory region of the At1g73160 gene of *Arabidopsis*. The said DNA sequence acts as a root-preferred promoter by conferring root-preferred expression of the GUS reporter gene cloned immediately downstream. Composition of the invention comprises a novel DNA sequence for a root-preferred promoter and the method comprises incorporation into the genome of a plant or plant cell, a DNA sequence operably linked to the said root-preferred promoter.

9 Claims, 4 Drawing Sheets
(3 of 4 Drawing Sheet(s) Filed in Color)

Fig.5 Promoter sequence(572bp) including 45bp coding sequence of gene At1g73160.(SEQ ID NO:1)

AGAAGAAGAAAGAGTTGTTCTTGAAGAATGGTTCTTGAAGGCCATTGTTTTGGTTTATTTGA
TTTTTGTGAATTGAGTGCAACTATTGATGTTGATTCTTTGCTTAAATTTCGGATCTTTCTCG
AGTTATTATATCAAAGTTCATTTCTCAATGACATTGCACATGGCTTAGCTAATTTTTATATG
GTTTTTACATTCAATTGAAAGTCAAATCTCTCTTAACCAACTGAGATTTGTAACTAAACCGG
GATATCACACCTAATTAGTTTTCCCGGTTTGATATTTTGTTTTGTACACGTAGGCGTGTGAT
TACTCCGTCACACTTTACACATGTGTAATTCCCCTAATTTATCGGGTTTCTTTAGGCGCGTG
AGATAATGCGCGTGTGTCTACGCTATTCTTGCGACGCTGTGCTTCCTAGGGTTTCGTCGTTG
CAAACACAGTCAATGTTCATGAACCACGGATCCTAATCTCCCCGATCTTCGATTCATTGTTT
CAGAAATCCCCAATTACTGTCTCTGTGCGTAAAATCTCTAGAGAAACCTTAAAATTTTCCGT
TCAGAGAAATTGTC

Fig.6 TAIL-PCR cloned sequence(SEQ ID NO: 2)

GATCCCAATGCCATTCTCTATATAAATTGTCGCAACCATGTGATGAAAAAACACAACAACCC
ATCTATACCATTTTTCTAGCTAAAATTAAACTAACACCTTTCTAAATTGAAACCATTGTCAC
ATAACACATGGCTAACTTGAAATTCTTGCTGTGCTTGTTCTTGATCTGCGTTTCCTTATCGC
GTTCATCAGCGTCTCGACCGATGTTCCCAAACGCAGACGGGATTAAACGAGGGCGTATGATG
ATAGAAGCAGAGGAAGTGTTGAAAGCGAGTATGGAGAAGCTAATGGAGAGAGGTTTTAATGA
GTCCATGAGACTCAGTCCTGGAGGTCCCGATCCTCGCCATCACTAAGTCTTATTCTCGTAGT
TTTGAATTCGAGGATGTATATTTTGTTCTTGATCGAGAACCGGTTTAGAAGAAAACATATCG
ATCCTCTTTGTTTGTTTTTTTTGCCTTGTTTGTTCGTTCGGTGTAACCAATATATTGATGTA
TCTGTTTCGTTACACATTTATGATTTGTGCATGCTTTACGTACCTTATACATTCCACTATAT
AGTAGTCTAGTAGAGAGGAGGACTTTGCATATAAATTGTTATATAACAAGAAAGGGTAAAGA
AATATAGTATGATAAGGGAGGATTGAATTAATTTAATTTATCCTGTTT

Fig. 7

DNA SEQUENCE FOR ROOT PREFERRED GENE EXPRESSION IN PLANTS

FIELD OF THE INVENTION

The invention described herein relates to the field of plant molecular biology in general and with particular reference to the control of gene expression in plants.

BACKGROUND OF THE INVENTION

The expression of a DNA sequence in plants requires a promoter that is immediately upstream of the DNA sequence and is functional in plants. The properties of the promoter determine the sites and timing of expression in the plant. A promoter that is constitutively active will direct expression in all cells and tissues of the plants whereas a promoter that is active in a preferred manner in certain cells and tissues will correspondingly direct expression in those parts of the plant. The function of a promoter is dependent upon the presence of a core promoter that usually comprises a TATA box and a transcriptional start site that directs RNA polymerase to initiate synthesis of RNA at a particular position for a given DNA sequence. The promoter may also comprise additional sequences that are generally located 5' but may also be located 3' to the core promoter, and regulate expression from the promoter. These additional sequences may comprise nucleotide sequences that act as enhancers or suppressors. Enhancers and suppressors are the DNA sites through which transcription activator and repressor proteins respectively exercise their regulatory effects on transcription. Enhancers and suppressors are known in the art and include for example the 35S enhancer element. DNA sequences comprising the core promoter and regulatory sequences may be included in transformation vectors for expression of desired DNA sequences in plants including tissue-preferred expression.

A number of promoters including tissue-preferred promoters have been identified in plants [Venkataraman et al, (2004) Mol. Genet. Genomics 270(5): 378–86; Furtado et al, (2003) Plant Mol. Biol. 52(4): 787–99; Trindade et al, (2003) Gene 303: 77–87; Liu J J and Ekramoddullah (2003) Plant Mol. Biol. 52(1): 103–20]. These include a root-preferred promoter (U.S. Pat. No. 6,518,483 B1). In addition promoter elements and corresponding DNA-binding proteins that are restricted to particular plant tissues have also been identified [Yin et al, (1997) EMBO J. 16(17): 5247–59; Yanagisawa and Sheen (1998) Plant Cell 10(1): 75–89]. It is considered of agronomic importance to acquire the ability to drive tissue-preferred expression of genes of interest in transgenic plants. For instance increased resistance to soil borne or root pathogens might be achieved through transformation of a plant by a DNA sequence that directs expression of a pathogen resistance gene under the control of a root-preferred promoter. As another instance, improved tolerance of a plant to abiotic stress such as water or salt stress may be facilitated by expression of a gene conferring tolerance in a part of the plant such as the root that may be particularly important with respect to that stress. Alternatively as another instance, root-preferred expression of a gene that causes root proliferation and increased root density may lead to higher and more efficient nutrient uptake by the root system.

It may also be desirable to inhibit the expression of a native DNA sequence in a plant in order to produce a particular phenotype. This inhibition may be achieved by expression of an antisense or dsRNA that interferes with expression of the native DNA sequence. It may be desirable to direct this expression in a tissue-preferred manner using a tissue-preferred promoter. Thus the ability to direct tissue-preferred expression of a DNA sequence of interest requires the development of a collection of tissue-preferred promoters that would drive expression in different tissues. It is also recognized by those skilled in the art that a single tissue-preferred promoter may show variation in the strength and degree of specificity of tissue-preferred expression when introduced into the genomes of different plant species. Hence it is also considered desirable by those skilled in the art to develop access to multiple tissue-preferred promoters that differ in their DNA sequence but show similarity with respect to their pattern of tissue-preferred expression, as one such promoter may perform better in a particular plant species than another promoter. Therefore isolation and characterization of additional tissue-preferred promoters including root-preferred promoters is desirable in order to carry out genetic manipulation of plants of agronomic interest.

The identification of genes showing tissue-preferred expression in plants is a first step towards isolation of the corresponding promoter regions from the genes and characterization of the promoter to test for tissue-preference of expression at the level of transcription. Genes showing tissue-preferred expression have been identified in plants using several different experimental approaches including a) subtractive hybridization [Crossley et al, (1995) *Planta* 196: 523–529.] b) differential cDNA screening [Kim Hyun Uk and Chung Tae Young (1997) Plant Mol. Biol. 33 (1): 193–198] and c) differential display RT-PCR [Song and Allen (1997) Biochim. Biophys. Acta 1351: 305–312].

An alternative strategy to identify tissue-preferred pattern of gene expression involves the use of enhancer detectors [Bellen (1998) Plant Cell 11(12): 2271–2281] which comprise a mobile genetic element (transposon or T-DNA) carrying a reporter gene that contains a minimal promoter. Insertion of the transposon in the genome nearby an enhancer sequence may confer expression of the reporter gene in a tissue-preferred manner that reflects the activity of the nearby enhancer. Enhancer detection using engineered maize Ds transposon elements called enhancer traps has been successfully applied in *Arabidopsis* plants to detect genes that are expressed in a tissue preferred manner [Sundaresan et al, (1995) Genes and Development 9(14): 1797–1810]. The identification of an Enhancer trap line showing a desired pattern of tissue-preferred expression is a starting point for isolation and characterization of the corresponding promoter region responsible for the tissue-preferred expression. Herein is described the isolation and characterization of a promoter that confers root-preferred expression. The sequence was identified based on analysis of an enhancer trap line of *Arabidopsis* showing root-preferred expression. The Ds transposon insertion in the line is in the *Arabidopsis* gene At1 g73160 that encodes a putative glycosyl transferase.

SUMMARY OF THE INVENTION

This invention relates to compositions and methods for directing tissue-preferred expression of nucleotide sequences in roots of a plant. The compositions of the present invention comprise a novel promoter sequence that directs transcription preferentially in roots, of a linked DNA sequence located immediately downstream of the promoter. This sequence has been isolated from the regulatory region of the *Arabidopsis* gene At1g73160 and comprises the nucleotide sequence (SEQ ID NO:1) given in FIG. 5, and any part of the sequence (SEQ ID NO:1) comprising at least 20 nucleotides. Compositions further comprise nucleotide sequences that share at least 70% identity to the sequence given in FIG. 5 or a part of that sequence. Compositions also comprise a plant or plant cell in which an expression cassette containing the said promoter driving expression of a DNA sequence, has been introduced into the genome. Also included in the compositions is the seed of such plants.

The methods of the present invention comprise the means to express a DNA sequence in a plant or plant cell by integration of an expression cassette into the genome of a plant or plant cell, wherein the said expression cassette comprises a promoter linked to the said DNA sequence, and the said promoter comprises a nucleotide sequence of the present invention.

DETAILED DESCRIPTION OF THE INVENTION

The present invention to compositions and methods for directing tissue-preferred expression of nucleotide sequences in roots of a plant. The compositions of the present invention comprise a novel promoter sequence that directs transcription preferentially in roots, of a linked DNA sequence located immediately downstream of the promoter. This sequence has been isolated from the regulatory region of the *Arabidopsis* gene At1g73160 and comprises the nucleotide sequence (SEQ ID NO:1) given in FIG. 5, and any part of the sequence (SEQ ID NO:1) comprising at least 20 nucleotides. Compositions further comprise nucleotide sequences that share at least 70% identity to the sequence given in FIG. 5 or a part of that sequence. Compositions also comprise a plant or plant cell in which an expression cassette containing the said promoter driving expression of a DNA sequence, has been introduced into the genome. Also included in the compositions is the seed of such plants.

Accordingly, the main embodiment of the present invention relates to a promoter sequence for root preferred gene expression in plants, wherein the promoter having at least 70% sequence homology to SEQ ID NO:1.

Yet another embodiment of the present invention is a promoter sequence as claimed in claim 1, wherein the promoter sequence is obtained from the upstream regulatory region of At1g73160 gene of *Arabidopsis*.

Still another embodiment of the present invention is a method of introducing root preferred gene expression in a plant using a promoter having at least 70% sequence homology to SEQ ID NO:1, said method comprising steps of:
  a. constructing an expression cassette containing the said promoter, operably linked upstream to a gene that is desired for preferred-expression in root,
  b. integrating the expression cassette into genome of the plant, and
  c. expressing the desired gene in the root of the plant by preferred expression.

In yet another embodiment of the present invention, the method provides improved resistance to soil borne pathogens.

Still another embodiment of the present invention is an expression cassette comprising a promoter having at least 70% sequence homology to SEQ ID NO:1, operably linked upstream to a gene that is desired for preferred-expression in root.

Yet another embodiment of the present invention is a plant cell comprising an expression cassette of claim 5, and a plant thereof.

BRIEF DESCRIPTION OF THE ACCOMPANYING DRAWINGS

The patent file contains at least one photograph executed in color. Copies of this patent with color photographs will be provided by the U.S. Patent and Trademark Office upon request and payment of the necessary fee.

FIG. 2: Analysis of *Arabidopsis* line ETC60 showing: i) presence of the Ds transposon in single copy in the genome, and ii) that the sequence amplified and cloned from genomic DNA of ETC60 using TAIL-PCR is identical to sequences flanking the site of insertion of the Ds transposon in the genome of line ETC60. A) Southern hybridization analysis of genomic DNA from ETC60 digested with EcoRI and probed with transposon sequences: EcoRI cuts twice within the transposon; the 2.6 kb band corresponds to an internal fragment within the transposon and the 3 kb and 6.5 kb bands correspond to the two junction fragments. B) Southern hybridization analysis of genomic DNA sequence from ETC60 as well as wild type Col and Landsberg strains digested with EcoRI and probed with cloned TAIL-PCR product from ETC60: Lane 1, Col DNA; Lane 3, ETC60 DNA; Lane 5, Landsberg DNA. The presence of a 2.2 kb band in ETC60 DNA and its absence in Col and Landsberg DNA indicates that the probe represents sequences flanking the site of transposon insertion in ETC60. Furthermore the absence of a wild type 4.5 kb band in ETC60 indicates that the plant used was homozygous for the transposon insertion.

DETAILED DESCRIPTION OF THE INVENTION

The identification of root-preferred promoters is considered desirable for genetic manipulation of plants of agronomic importance. For instance expression of a pathogen resistance gene preferably in roots can be used to engineer plants for resistance against soil-borne or root pathogens. Alternatively expression of a gene that confers tolerance to abiotic stress such as water or salt stress, preferentially in those tissues such as the root which may be of most importance with respect to that stress can be used to confer tolerance to abiotic stress.

Figure 4:
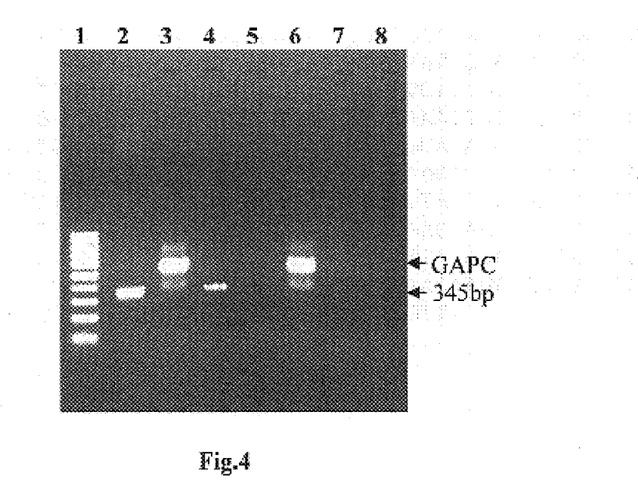
FIG. 4: RT-PCR analysis of expression of At1g73160 showing root-preferred expression: Lane 1, 100 bp DNA marker; Lane 2, *Arabidopsis* genomic DNA amplified with gene specific primers (GLTF and GLTR) for At1g73160; Lanes 3, 6: PCR on samples of *Arabidopsis* root and leaf cDNA respectively, with control GAPC primers. Lanes 4, 5: PCR on *Arabidopsis* root and leaf cDNA respectively of *Arabidopsis*, with gene specific primers GLTF and GLTR for At1g73160. Lanes 7, 8: PCR on samples of *Arabidopsis* root and shoot RNA respectively showing absence of amplification as a negative control.
Figure 5:
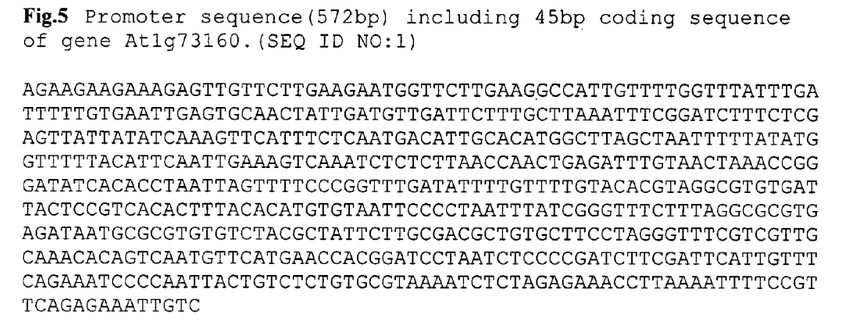
FIG. 5: 572 bp including 527 bp upstream sequence of At1g73160, showing root-preferred promoter activity (SEQ ID NO:1).

This invention comprises novel DNA sequences for a "root-preferred promoter" from the At1g73160 gene of *Arabidopsis*. The At1g73160 gene encodes a putative glycosyl transferase and is preferentially expressed in roots (FIG. 4). In particular the invention comprises a DNA molecule containing the sequences given in FIG. 5, and parts or variations of those sequences. A "part" of the disclosed DNA sequence may retain biological activity and hence be capable of driving root-preferred expression of a DNA sequence that is placed immediately downstream. A "part" of the DNA sequence may range from at least 20 nucleotides, about 50 nucleotides, about 200 nucleotides, and up to the full-length nucleotide sequence of the present invention. A "part" of the At1g73160 promoter may encode a biologically active portion of the promoter or it may be a fragment that can be used as a hybridization probe or a primer for PCR using methods disclosed below. A biologically active portion of the At1g73160 promoter can be prepared by isolating a part of the At1g73160 promoter sequence of the present invention and determining the activity of that portion of sequence. DNA molecules that are part of the At1g73160 promoter comprise at least 16, 20, 50, 75, 100, 150, 200, 250, 300, 350, 400, 500 nucleotides or up to the number of nucleotides present in the full-length promoter sequence disclosed herein (FIG. 5).

By a "variation" of the sequence is meant a sequence that is substantially similar. Variations that occur naturally can be identified using known techniques such as hybridization and PCR. Variations also include synthetically derived nucleotide sequences such as those obtained by site-directed mutagenesis. Variations of a particular nucleotide sequence will have at least 40%, 50%, 60%, 70%, 80%, 90% and up to 98% or more sequence identity to that particular sequence as determined by methods for alignment of sequences. Such methods are well known in the art and may include but are not limited to the algorithm of Myers and Miller (1988) CABIOS 4: 11–17; the method of Pearson and Lipman (1988) Proc. Natl. Acad. Sci. USA 85(8): 2444–2448; and the algorithm of Karlin and Altschul (1993) Proc. Natl. Acad. Sci. USA 90(12): 5873–5877. Computer implementations of these mathematical algorithms can be utilized for sequence comparison and include but are not limited to: CLUSTAL in the PC/Gene program; the ALIGN program (version 2.0), and BLAST in the Wisconsin Genetics Software Package, Version 8. Alignments using these programs can be performed using the default parameters. BLAST nucleotide searches can be performed with the BLASTN program, score=100, word length=12 (see the BLAST link on the National Center for Biotechnology Information website, maintained by the National Institutes of Health, Bethesda, Md., USA). Alignment may also be performed by inspection. For the purposes of the present invention, comparison of DNA sequences for determination of percent sequence identity to the At1g73160 promoter is preferably made using the BLASTN program (version 2.0 or later).

Figure 7:
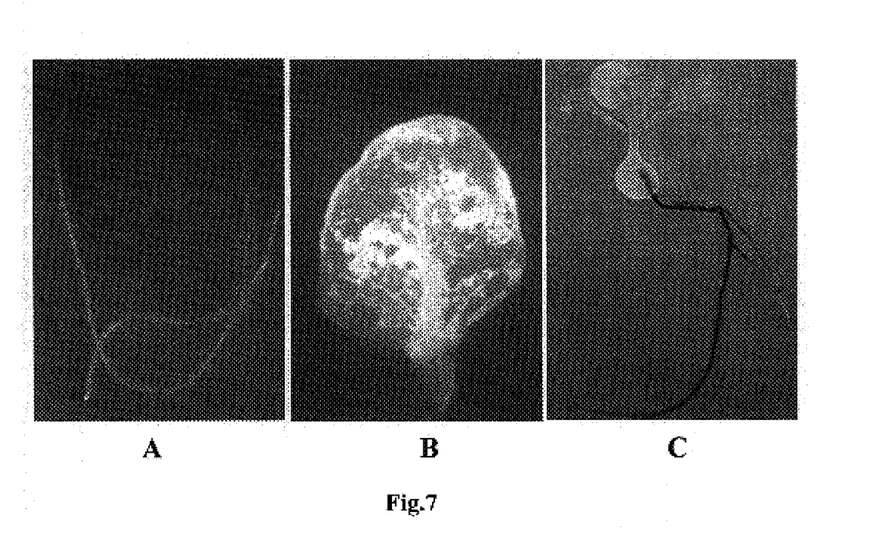
FIG. 7: Root-preferred expression of the GUS reporter gene in a *Arabidopsis* line transformed with pBI101.1::U1 (see Example 9 below). A) Expression of the GUS reporter in roots of a primary T1 transformant; B) Leaf of the same T1 transformant as in A stained with X-Gluc showing absence of GUS expression; C) Whole T2 seedling grown from the seed of the T1 transformant stained with X-Gluc showing root preferred expression.

The promoter sequences of the At1g73160 gene when positioned immediately upstream of a GUS reporter gene direct the expression of the GUS gene in a root-preferred manner (FIG. 7). Hence the promoter of the At1g73160 gene may be used for root-preferred expression of a DNA sequence of interest. Biologically active variations of the At1g73160 promoter are also included in the present invention. Variation also encompasses sequences derived from procedures involving mutagenesis and recombination such as DNA shuffling. With such a procedure, one or more different At1g73160 promoter sequences can be manipulated to create a new At1g73160 promoter possessing the desired properties. Such procedures are known in the art. For example, see Stemmer (1994) Proc. Natl. Acad. Sci. USA 91(22): 4504–4509; Zhang et al. (1997) Proc. Natl. Acad. Sci USA 94(9): 4504–4509; and U.S. Pat. Nos. 5,605,793 and 5,837,458.

The DNA sequences of the present invention can be used to isolate the corresponding sequences from other organisms, particularly from other plants. Such sequences may be identified based on their homology to all or part of the At1g73160 promoter sequence by using methods such as PCR or hybridization. Sequences isolated based on their sequence identity to all or part of the At1g73160 sequence given in FIG. 5 are also encompassed by the present invention.

For the purpose of PCR, oligonucleotide primers can be designed for amplification of corresponding DNA sequences using either genomic DNA or cDNA extracted and prepared from a plant. Methods for the design of PCR primers and cloning of PCR products are well known in the art and are given in Sambrook et al, (1989) Molecular Cloning: A Laboratory Manual (2d ed., CSHL Press, Plainview, N.Y.) and in Innis et al., eds. (1990) PCR Protocols: A Guide to Methods and Application (Academic Press, N.Y.).

The technique of hybridization uses the entire amount or a part of a nucleotide sequence as a probe that hybridizes selectively to corresponding sequences present in a population of cloned cDNA or genomic DNA fragments (cDNA or genomic DNA libraries) from an organism of interest. The hybridization probe may be prepared using all or part of a genomic DNA or cDNA sequence or an oligonucleotide and may be labeled with a detectable moiety including but not limited to 32 p, digoxigenin, or biotin. Methods for preparation of hybridization probes are well known in the art and are given in for example Sambrook et al. (1989). In the present case the entire At1g73160 promoter sequence (SEQ ID NO:1) region given in FIG. 5 or a part thereof may be used as a probe capable of hybridizing to corresponding promoter sequences from an organism of interest. Such probes include sequences that are unique to the At1g73160 promoter sequences and are preferably at least 10 nucleotides in length and most preferably at least about 20 nucleotides in length. Such probes may be used to amplify sequences corresponding to the At1g73160 promoter from other plants. This technique may be used to isolate additional coding sequences from a plant of interest or used as a diagnostic test for the presence of coding sequences in a plant.

Hybridization may be conducted under stringent conditions. By "stringent" is meant conditions under which the probe hybridizes to its target sequence to a measurably greater extent than to other unrelated sequences, for example preferably at least 2-fold greater. Generally stringent conditions will be those in which the salt concentration is less than about 1.5 M Na$^+$ ion, typically about 0.01 to 1.0 M Na$^+$ ion concentration (or equivalent concentration of other salts) at pH 7.0 to 8.4 at a temperature of at least about 30° C. for short probes (e.g. 10 to 50 nucleotides) and at least about 60° C. for long probes (greater than 50 nucleotides in length). Stringent conditions can also be attained using a destabilizing agent such as formamide. Low stringency conditions include hybridization in a buffer solution containing 30 to 35% formamide, 1 M NaCl, 1% SDS at 37° C. and a wash in 1× to 2×SSC (20×SSC=3.0 M NaCl/0.3 M trisodium citrate) at 50 to 55° C. Moderate stringency conditions include hybridization in a buffer containing 40 to 45% formamide, 1.0 M NaCl, 1% SDS at 37° C. and a wash in 0.5× to 1×SSC at 55 to 60° C. High stringency conditions include hybridization in 50% formamide, 1 M NaCl, 1% SDS at 37° C. and a wash in 0.1×SSC at 60 to 65° C. Duration of hybridization is generally about 4 to 16 hours.

Specificity of hybridization is generally achieved by the stringency of post-hybridization washes and is determined by the ionic strength and temperature of the final wash solution. The $T_m$ is the temperature (for a given ionic strength and pH) at which 50% of a complementary target sequence hybridizes at equilibrium to a perfectly matched probe. For DNA-DNA hybrids, the $T_m$ can be approximated by the formula: $T_m=81.5°$ C.$+16.6(\log M)+0.41(\% GC)-0.61(\%$ formamide$)-500/L$ where M is the molarity of monovalent cat ions, %GC is the percentage of guanosine and cytosine nucleotides in the DNA, % formamide is the percentage of formamide in the hybridization solution, and L is the length of the hybrid in base pairs. For each 1% of mismatch, $T_m$ is reduced by about 1° C. Hence $T_m$, hybridization, and wash conditions can be adjusted for the probe to hybridize to sequences of the required identity. For example, if sequences with ≧85% identity are desired, the $T_m$ can be decreased by 15° C. Generally, high stringent conditions are chosen so as to be about 5° C. lower than the $T_m$ for the specific sequence and its complement at a defined ionic strength and pH. Moderately stringent conditions can use a temperature of hybridization and/or washes that is between 6 and 10° C. lower than the $T_m$, whereas low stringency conditions employ a hybridization and/or washing at between 11 and 20° C. lower than the $T_m$. Hence isolated sequences having biological activity as promoters and which hybridize under stringent conditions to the At1g73160 promoter are encompassed by the present invention. Such sequences will have sequence identity that ranges from at least 40% to 50%, about 60% to 70%, and even about 75%, 80%, 85%, 90%, 95% to 98% or more with the sequences given in the present invention.

The promoter sequences of the present invention may be used to express a DNA sequence of interest, thereby leading to a change in phenotype of the plant. Changes in phenotype that are of interest include modifying expression of one or more genes in a plant root, changing the defense mechanism of a plant against a pathogen or insect, altering tolerance to a herbicide, and modifying root development to better adapt to environmental stress. These effects can be attained by expression of heterologous DNA sequences or by altering expression of one or more endogenous sequences.

Types of genes of interest for expression using the promoter of the present invention include but are not limited to transcriptional regulators such as MADS box transcription factors [Parenicova et al, (2003) Plant Cell 15: 1538–51] signal transduction molecules such as kinases [Verica et al, (2003) Plant Physiol. 133 (4): 1732–46] and other genes encoding agronomically important traits such as disease resistance, insect resistance, herbicide resistance, and increased nutrient uptake. Disease resistance genes may include avirulence (avr) and resistance (R) genes [e.g. Jones et al, (1994) Science 266: 789–93], and others. Insect resistance genes may encode resistance to pests such as rootworm and cutworm. Such genes include but are not limited to Bacillus thuringiensis toxic protein genes [e.g. Geiser et al, (1986) Gene 48(1): 109–18; U.S. Pat Nos. 5,366,892; 5,747.450; 5,737,514; 5,723,756; 5,593,881], and lectins [e.g. Van Damme et al, (1994) Plant Mol. Biol. 24(5): 825–30]. Genes encoding herbicide resistance traits include but are not limited to acetolactate synthase (ALS) carrying S4 and or Hra mutations [Andrej Kochevenko and Lothar Willmitzer (2003) Plant Physiol. 132: 174–184], genes coding for resistance to phosphinothricin (e.g. the bar gene) (Lutz K A, Knapp JE, and Maliga P. (2001) Plant Physiol. 125(4): 1585–90), or other genes. Genes encoding nutrient uptake components include but are not limited to ATK1, a component of the potassium uptake system in Arabidopsis [Spalding et al, (1999) J. Gen. Physiol. 113: 909–18], PHO1, a phosphate transporter [Hamberger et al, (2002) Plant Cell 14(4): 889–902] and CHL3, a nitrate transporter [Wilkinson and Crawford (1991) Plant Cell 3(5): 461–71]. It is apparent that any gene of interest or fragment thereof can be operably linked to the promoter sequences described in the present invention and expressed in plant roots.

The promoter sequence disclosed herein may also be useful in inhibiting the expression of a target gene in order to achieve a desired phenotype or to direct the expression of an antisense oligonucleotide of interfering RNA (RNAi) that blocks expression of a target gene. The antisense oligonucleotide encodes an RNA molecule that is complementary and capable of hybridizing to the messenger RNA (mRNA) of the target gene. The binding of antisense RNA inhibits formation of the protein encoded by the target gene. Inhibition of formation of the target protein can also be achieved by operably linking a sequence that contains two regions, one of which is homologous to a portion (or all) of the target gene and the other is complementary to the former region. The two regions therefore have the potential to self-anneal and form a double-stranded RNA molecule (dsRNA). dsRNA is known in the art to lead to the inhibition of expression of the target gene and/or inhibition of production of the target protein [Golovkin and Reddy (2003) Plant Physiol. 132(4): 1884–91].

In following this approach, modifications of the antisense or dsRNA sequences can be made so long as the sequences still hybridize to and inhibit the expression of the corresponding mRNA and/or protein. The identity of the antisense or dsRNA to the sequence of the target gene may be 70%, preferably 80%, and more preferably 85% or more. The length of the antisense or dsRNA oligonucleotides may be at least 50 nucleotides, 100 nucleotides, 200 nucleotides or more. By these means, antisense DNA sequences or sequences encoding dsRNA may be operably linked to the sequences of the present invention and used to inhibit expression of a protein of interest in the plant root.

The regulatory sequences of the present invention confer root-preferred expression of an operably linked DNA sequence when integrated into the genome of a plant. By "root-preferred" is intended that the expression is most abundant in the root. By root is meant any portion of the root structure including but not limited to primary root, lateral root, the root cap, root apex, root meristem, protoderm, ground meristem, endodermis, cortex, and epidermis. While some level of expression of the heterologous nucleotide sequence may occur in other tissue of the plant, most abundant expression is observed in the root.

By "heterologous nucleotide sequence" is meant a sequence that does not naturally occur with the promoter of the present invention. The sequence may however be homologous, or native, or heterologous, or foreign to the host plant.

It is known in the art that enhancer sequences may be used to increase levels of transcription. Hence it is recognized that enhancers may be used in combination with the present invention to increase transcription. Other modifications of the present invention may also be used, including sequences that increase or decrease the degree of expression.

The nucleotide sequences of the present invention as well as parts and variations of the same DNA, when operably linked to a DNA sequence, are useful in controlling expression of that sequence when stably integrated into the genome of a plant. By "operably linked" is meant that the expression of the DNA sequence is directly under the influence of the promoter sequence. By "operably linked" is also intended the connection of the two DNA sequences such that the two are contiguous with one another and that the coding sequence of each of the two sequences retains the correct reading frame. By this means the DNA sequences of the present invention may be used to construct an expression cassette along with heterologous DNA sequences for expression in a plant of interest, in particular in roots of the plant.

The expression cassette will contain a transcriptional initiation region comprising the promoter DNA sequences of the present invention or parts or variations thereof, operably linked to a heterologous nucleotide sequence. The expression cassette may also contain selectable marker genes. The expression cassette will contain in a 5'-to-3' direction of transcription, a region that directs transcriptional initiation, a region that directs translational initiation, and a region that directs translational and transcriptional termination. The region directing termination associated may be native with the transcriptional initiation region comprising the promoter DNA sequences of the present invention. Alternatively the terminating region may derive from elsewhere. Commonly used terminating regions derive from the Ti-plasmid of *Agrobacterium tumefaciens* such as octopine synthase and nopaline synthase terminating regions. The expression cassette may include additional modifications to increase gene expression. These include but are not limited to elimination of sequences encoding spurious polyadenylation signals, intron-exon splice junctions, stem-loop structures, hairpin structures, and transposon-like repeats. The expression cassette may additionally contain 5' leader sequences in the expression construct. 5' leader sequences are known in the art to increase translation.

Reporter genes or selectable marker genes may be included in the expression cassette. Examples of reporter genes are known in the art and can be found in for example Jefferson et al, (1991) in Plant Molecular Biology Manual ed. Gelvin et al, (Kluwer Academic Publishers) pp. 1–33. Selectable marker genes for selection of transformed cells or tissues can include genes that confer resistance to an antibiotic or herbicide. Examples of selectable marker genes used in plant transformation include but are not limited to: chloramphenicol [Herrera-Estrella et al, (1983) EMBO J. 2: 987–995]; hygromycin [Waldron et al, (1985) Plant Mol. Biol. 5: 103–108]; methotrexate [Herrere-Estrella et al, (1983) Nature 303: 209–213]; phosphinothricin [DeBlock et al, (1987) EMBO J. 6: 2513–2518], kanamycin [Chabaud et al, (2003) Plant Cell Rep. 22(1): 46–51].

The expression cassette comprising the promoter sequence of the present invention operably linked to a DNA sequence of interest can be used to transform any plant of interest. By this means genetically modified plants, plant tissues, and plant cells carrying the promoters sequences stably integrated into the plant genome may be obtained.

Plant species of interest that may be transformed by the expression cassette containing promoter sequences of the present invention include but are not limited to: *Brassica* sp., Rice, Cotton, Mango, Wheat, Corn, Oats, Barley, Tobacco, Ginger, Potato, Sugarcane, Sugar beet, Carrot and Tomato. Protocols and procedures for plant transformation may vary depending upon the plant species and type of plant tissues. Methods for transformation of plant cells with DNA include but are not limited to micro particle bombardment [for example, Christou et al, (1988) Plant Physiol. 87: 671–674 (Soybean)], *Agrobacterium* mediated transformation [Sonia Tingay et al, (1997) The Plant Journal 11(6) 1369–1376; Hinchee MAW et al, (1988) Bio/Technol. 6: 915–922], electroporation [see for example Riggs et al, (1986) Proc. Natl. Acad. Sci. USA 83: 5602–5606], microinjection [see for example Crossway et al, (1986) Bio-techniques 4: 320–334], and direct gene transfer [Potrykus et al, (1985) Mol. Gen. Genet 199: 183–188]; all of these are incorporated herein by reference. Plant cells that have been transformed may be grown into plants using methods that are well known in the art. See for eg. Gordon-Kamm, W. et al, (1990) Plant Cell 2(7): 603–618. Such plants may then be grown and pollinated with either the same strain or with a different strain to produce seeds. The seeds may then be grown into plants and those plants having root-preferred expression of the desired phenotype or nucleotide sequences may be identified.

EXPERIMENTAL

The promoter region of the At1g73160 gene was isolated from *Arabidopsis* genomic DNA. The sequence for the promoter is given in FIG. 5. The isolation and characterization of the promoter is described as follows.

EXAMPLE 1

Generation and Screening of a Collection of Enhancer and Gene Trap Lines of *Arabidopsis*

A collection of 450 independent enhancer trap and gene trap lines of *Arabidopsis* were generated as described in Sundaresan et al, (1995) Genes and Development 9:1797–1810. These lines were generated by crossing two *Arabidopsis* starter lines one of which carried an immobilized Ac element (Activator line) and the other carried a single copy of a Ds element: either an enhancer trap (DsE) or gene trap (DsG). The DsE construct comprised a plant selectable NPT II gene driven by a 1'NOS promoter and a GUS reporter gene under control of a minimal promoter derived from the −1 to −46 region of the CaMV 35S promoter both of which were contained within the Ds element. In addition each starter line also carried the IAAH gene driven by the 2'NOS promoter on the same T-DNA as the Ac or Ds element but outside the transposon. The IAAH gene confers sensitivity to the proauxin α-Naphthyl Acetamide (NAM). The DsG construct was similar to DsE but instead of a minimal promoter driving GUS, it contained a promoter-less GUS gene with an intron fused upstream of GUS ATG codon and the addition of a triple splice site acceptor.

The F1 plants were grown and F2 seeds were collected. Approximately 1000 F2 seeds from each F1 plant were surface sterilized by successive washes (3 minutes each) in 95% ethanol, 0.025% mercuric chloride, and 4 changes of sterile water. The seeds were suspended in 10 ml of top agar containing selective medium (MS medium containing 2% sucrose, 50 µg/ml Kanamycin, and 3.5 µM NAM) and plated on 150 mm plates containing selection medium. The plates were kept at 4° C. for 4 days and transferred to illuminated growth racks at 23° C. for 5 days. Seedlings resistant to both NAM and Kanamycin were identified by their green colour and elongated roots and transferred to small (60 mm) selection plates to verify their phenotype. A single Kan$^R$ NAM$^R$ plant per F2 family was transferred to soil and F3 seed were collected.

EXAMPLE 2

Screening of Enhancer Trap and Gene Trap Lines for Root-Preferred Expression

Between 10–15 F3 seeds of enhancer trap and gene trap lines were surface sterilized by soaking them in 95% ethanol for 10 minutes and for 3 minutes in 0.05% HgCl$_2$ and were washed with sterile distilled water five times before plating on to 0.7% MS agar medium (Sigma chemicals # M-5519, St. Louis, Mo., USA) supplemented with 50 µg/ml Kanamycin. Seeds were subjected to vernalisation at 4° C. for 48 hours and were shifted to growth chamber set at 20° C. with 16 h light and 8 h dark cycle regime.

Figure 1:
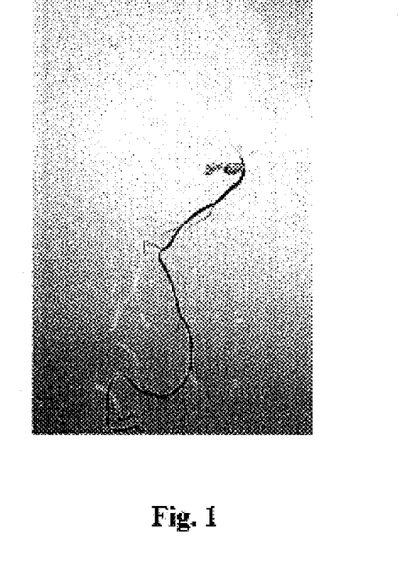
FIG. 1: Seedling of *Arabidopsis* gene trap line ETC60 stained with X-Gluc showing root-preferred expression of the GUS reporter gene.

Kanamycin resistant transposant seedlings at 4-leaf stage were screened for GUS expression pattern. Individual seedlings representing each line were placed in 24-well micro titer plates and immersed in about 750 µl of GUS-staining solution (2 mg/ml 5-bromo-4-chloro-3-indolyl-beta-D-glucuronic acid in 0.1 M sodium phosphate pH 7.0, 0.1% Triton-X-100, 0.5 mM K$_3$FeCN$_6$, 0.5 mM K$_4$FeCN$_6$, 10 mM Na$_2$EDTA). These plates were kept in a desiccator and a vacuum of 650–700 mm Hg was drawn. Samples were subjected twice to vacuum each for 10–15 minutes. Treated samples were placed in a plastic box laid with wet paper towels at its base and incubated at 37° C. for 16–18 hours. The GUS expression in roots was detected by blue colour, which results from the enzymatic cleavage of X-GLUC by β-glucuronidase. After staining, samples were cleared from chlorophyll by several changes of 70% ethanol at 37° C. One Enhancer trap line designated as ETC60 was identified that showed root specific GUS expression pattern. Expression was not detected in aerial parts of the plant (FIG. 1). This line was chosen for the isolation of root-preferred promoter.

EXAMPLE 3

Isolation of Flanking DNA Sequences from a DsE Insertion Line (ETC60) Showing Root-Preferred Expression a) Genomic DNA Isolation from the *Arabidopsis* Plants:

1–5 g plant tissue from the ETC60 line was macerated in a pool of liquid nitrogen in a pre-cooled mortar until powdered. Freshly prepared 1 ml extraction buffer (100 mM Tris pH 8.0; 50 mM EDTA pH 8.0; 500 mM NaCl; 10 mM 2-Mercaptoethanol and supplemented with 3.5 ml of 20% SDS per 50 ml buffer) was added slowly and mixed. Tissue was transferred to a centrifuge tube containing 3 ml ice-cold extraction buffer. The sample was vortexed for 5–10 seconds and centrifuged at 8000 rpm for 10 minutes. Equal volume 2× CTAB buffer [2% CTAB (w/v), 100 mM Tris pH 8.0, 20 mM EDTA pH 8.0, 1.4 M NaCl] was added to the supernatant in a fresh tube, mixed, and incubated at 65° C. for 5 minutes. Approximately equal volume of Chloroform:Isoamyl alcohol (24:1) was added, vortexed and spun at 6000 rpm for 10 minutes at room temperature (RT). 0.6 volumes of isopropanol was added to the saved aqueous phase, mixed and spun at 8000 rpm for 10 minutes at RT.

The pellet was resuspended in 400 µl TE [10 mM Tris, 1 mM EDTA (pH 8.0)] and the contents were transferred to a 1.5 ml eppendorf tube. DNAse-free RNAse (50 µg/ml) was added and incubated at 37° C. for 10 minutes. The sample was extracted once with phenol: chloroform (1:1) followed by a chloroform extraction. Adding 0.1 volumes of 3 M Sodium-acetate pH 5.5 and 2.5 volumes of redistilled ethanol precipitated DNA. The sample was spun at 14000 rpm. The pellet was washed thrice in cold 70% ethanol allowing 20 minutes incubation followed by a one-minute spin at 10,000 rpm each time. The pellet was air dried and resuspended in 100–200 µl TE and stored at −20° C. until use.

b) Isolation of Flanking DNA Sequences from the Site of DsE Insertion:

5' flanking genomic DNA sequences of DsE were amplified by following the TAIL-PCR procedure as described by Liu et al., Plant Journal (1995) 8: 457. The primers employed were AD2 (Arbitrary Degenerate primer) and Ds5–1, Ds5–2 and Ds5–3 specific to the 5' end of the DsE transposon. Primer sequences are as follows;

Primer Sequences:

```
AD2:
5'-NGT CGA (G/C)(A/T)G ANA (A/T)GAA-3' (SEQ ID NO:3)

Ds5-1:
5'-CCG TTT ACC GTT TTG TAT ATC CCG-3' (SEQ ID NO:4)

Ds5-2:
5'-CGT TCC GTT TTC GTT TTT TAC C-3'    (SEQ ID NO:5)

Ds5-3:
5'-GGT CGG TAC GGA ATT CTC CC-3'       (SEQ ID NO:6)
```

A primary PCR involving 60 pmole AD2 and 4 pmole Ds5–1 primers was set up in 20 µl volume containing 75–100 ng ETC60 genomic DNA, 1×PCR buffer [50 mM KCl, 10 mM Tris-HCl, pH 8.3, 1.5 mM MgCl$_2$ and 0.001% (w/v) gelatin] 200 µM each of dATP, dTTP dGTP and dCTP and 5 units of Taq polymerase. The program followed for the primary PCR was 95° C. 2 min; 5 cycles of 94° C. 30 sec., 62° C. 1 min, 72° C. 2.5 min; 1 cycle of 94° C. 30 sec., 25° C. 3 min, ramp to 72° C. 3 min, 72° C. 2.5 min; 15 super cycles of 94° C. 10 sec., 68° C. 1 min, 72° C. 2.5 min, 94° C. 10 sec., 68° C. 1 min, 72° C. 2.5 min, 94° C. 10 sec., 44° C. 2.5 min; 72° C. 5 min, 4° C. soak. Primary PCR product was diluted 1 µl in 50 µl in water. 1 µl of diluted primary PCR product was used for secondary PCR reaction.

Secondary PCR was set up in 20 µl reaction volume containing 1 µl diluted PCR product of primary PCR reaction, 1×PCR buffer [50 mM KCl, 10 mM Tris-HCl, pH 8.3, 1.5 mM MgCl$_2$ and 0.001% (w/v) gelatin], 200 µM each dNTPs, 4 pmole Ds5–2, 40 pmole AD2 and 5 units of Taq polymerase. The cycling conditions used for secondary PCR was 15 super cycles of 94° C. 10 sec., 64° C. 1 min, 72° C. 2.5 min, 94° C. 10 sec., 64° C. 1 min, 72° C. 2.5 min, 94° C. 10 sec., 44° C. 1 min, 72° C. 2.5 min; this was followed by 72° C. for 5 min and a soak at 4° C. The secondary PCR product was diluted 1 µl in 50 µl water.

Tertiary PCR was set up in 20 µl reaction volume containing 1 µl of diluted secondary PCR product, 1× PCR buffer (50 mM KCl, 10 mM Tris-HCl, pH 8.3, 1.5 mM MgCl$_2$ and 0.001% (w/v) gelatin), 200 µM each of dNTPs, 4 pmole Ds5–3, 40 pmole AD2 and 5 units of Taq polymerase. The cycling conditions used for tertiary PCR was 94° C. 15 sec., 44° C. 1 min, 72° C. 2.5 min for 30 cycles; 72° C. 5 min followed by a 4° C. soak.

15 µl of the secondary and the tertiary products were run on a 3% TAE agarose gel at 150 volts for 1 hour. A 71 bp difference was detected between the secondary and tertiary TAIL PCR products corresponding to the difference between the distance between the Ds5–2 and Ds5–3 sequences in the transposon. Secondary TAIL-PCR reaction was used in blunt end cloning. An amplicon of 668 bp was cloned in pTOPO II, a blunt-end cloning vector (Invitrogen) following the manufacturer's protocol. Recombinant plasmid was isolated using plasmid miniprep kit (Qiagen) according to the manufacturers' instructions. The purified DNA was then sequenced with M13 forward primer (5'-CGCCAGGGTTTTCCCAGTCACGAC-3') (SEQ ID NO:7) using an automated DNA sequencer ABI 3700 (ABI, Foster City, USA).

EXAMPLE 4

Southern Analysis of ETC60 a) Genomic Southern Hybridization to Determine Copy Number of DsE Element

The protocol for Southern Hybridization was essentially as described in Sambrook et al, 1989. Genomic DNA was isolated as described in Example 3a from the ETC60 line and from Landsberg erecta (Ler). Two to three micrograms of genomic DNAs of ETC60 and Ler were digested with EcoR1 and separated electrophoretically on a 0.7% agarose/TAE gel, denatured, neutralized, and transferred to Hybond N membranes (Amersham Life Science, Buckinghamshire, England) by capillary transfer. DNA was cross-linked to the membrane using a UV Stratalinker (Stratagene, La Jolla, Calif., USA).

Figure 6:
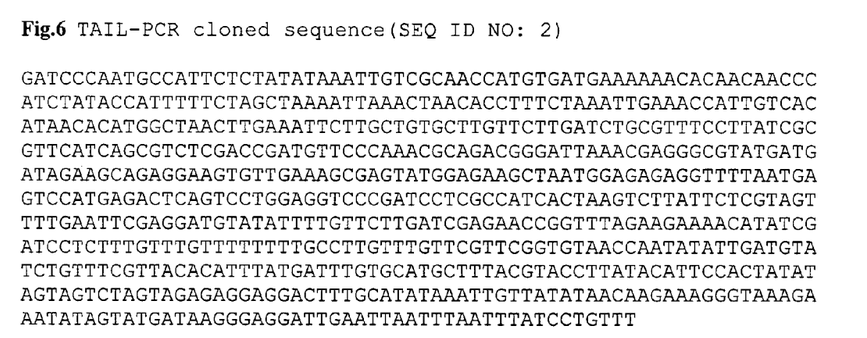
FIG. 6: Sequence of the TAIL-PCR product obtained from *Arabidopsis* line ETC60 and cloned in to pTOPOII (Invitrogen) (SEQ ID NO:2).

The blot was pre-hybridized in a solution of 0.5 M Sodium phosphate buffer pH 7.2, 7% Sodium dodecyl sulphate (SDS), 1 mM EDTA for 4 h at 65° C. 75 ng of pWS31 a plasmid carrying the DsE construct was labeled with $\alpha^{32}$P-dATP using a random primer labeling kit (JONAKI-BRIT, Mumbai, India) as described by the manufacturer and the blot was hybridized with the labeled probe for 18 h at 65° C. with constant shaking. Blots were washed at 65° C. sequentially with 2×SSC (1×SSC=0.15 M Sodium chloride, 0.015M Sodium Citrate, pH 7.0), 0.5% SDS; 0.5×SSC/0.5% SDS; 0.2×SSC/0.5% SDS and finally with 0.1×SSC/0.5% SDS for 20 min each wash. Auto radiography was done by exposing the blot to X-Ray film at –70° C.

b) Southern Hybridization to Confirm the TAIL Clone:

In order to ascertain that the isolated TAIL-clone is genuine and did not arise spuriously, we used it as a probe against a blot containing EcoRI digested genomic DNAs of line ETC60, Col and Ler (WT) in order to detect the polymorphism between ETC60 and the Wild type *Arabidopsis* parents. ETC60 was derived from Columbia and Landsberg erecta (Ler.). Probe (PCR amplification product of sequence shown in FIG. 6) was labeled with $\alpha^{32}$ 32PdATP in a PCR reaction using M13 forward (SEQ ID NO:7) and reverse primers (5'-AGCGGATAACAATTTCACACAGGA-3') (SEQ ID NO:8). PCR reaction was set up in 20 µl volume containing 1×PCR buffer (50 mM KCl, 10 mM Tris-HCl, pH 8.3, 1.5 mM MgCl$_2$ and 0.001% (w/v) gelatin), 200 µM each of dTTP, dGTP, and dCTP, 50 µM dATP, 20 µCi $\alpha^{32}$P-dATP. PCR was carried out for 30 cycles of 94° C. for 20 sec., 55° C. for 30 sec., 72° C. for 2 min., followed by a soak at 4° C.

Unincorporated label was removed by gel filtration through a Sephadex G-50 spin column. The blot was hybridized with the denatured probe at 65° C. for 18 h with constant shaking. Blots were washed at 65° C. with 2×SSC (1×SSC=0.15 M Sodium Chloride, 0.015 M Sodium Citrate, pH 7.0), 0.1% SDS and 5 mM Sodium phosphate (pH 7.0) for 3×20 min and with 0.5×SSC, 0.1% SDS and 3 mM Sodium phosphate buffer (pH 7.0) for 3×20 min.

Figure 2:
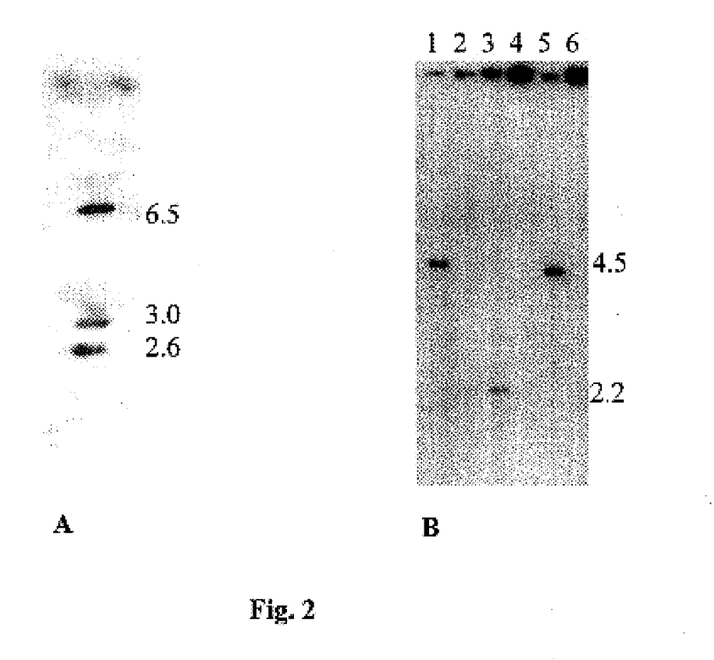

Autoradiography was done by exposing the blots to X-Ray film at –70° C. The RFLP obtained using the restriction enzyme EcoRI is depicted in FIG. 2B. A hybridized band of size 4.5 kb was detected in parental genomes (Col and Ler) whereas the size was 2.2 kb in line ETC60. The smaller fragment is due to a restriction fragment length polymorphism resulting from an additional EcoRI site in the transposon. The probe hybridization pattern revealed that, the clone is a genuine one and corresponds to the flanking genomic DNA sequence of the single DsE insertion (FIG. 2A) in line ETC60.

EXAMPLE 5

Determination of Nucleotide Sequence of Flanking DNA from ETC60

Figure 3:
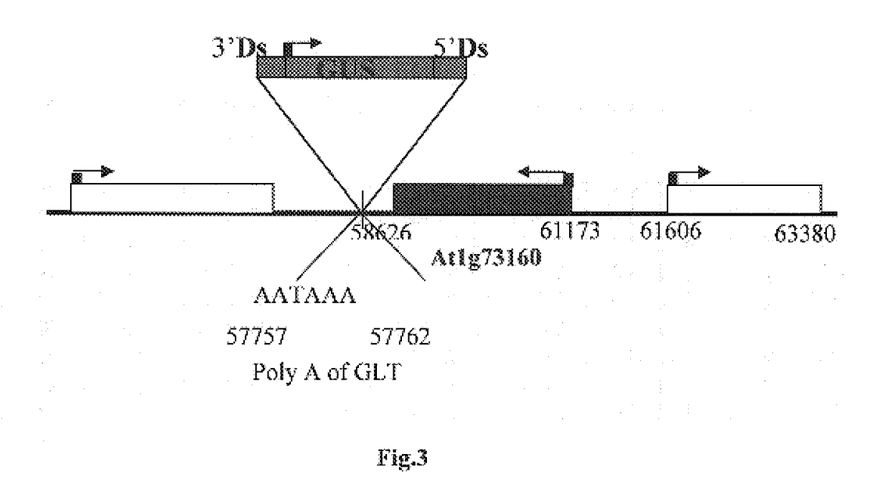
FIG. 3: Schematic showing position and orientation of Ds insertion with respect to DNA coordinates of BAC clone T18K17 from chromosome 1 of *Arabidopsis*. The insertion is in the 3' UTR of the putative gene At1g73160.

The sequence of the TAIL-PCR clone was used in homology search against the *Arabidopsis* sequence database with the help of the BLASTN algorithm (Altschul et al, 1997. Nucleic Acids Res. 25: 3389–3402) through the web site of the National Center for Biotechnology Information, Bethesda, Md., USA. A strong homology of 100% (194/194 bp) identity was found to part of a BAC clone, T18K17 from chromosome 1. The genomic map position of the insertion was derived based on the sequence alignment of the BAC clone and TAIL clone using the BLAST2 algorithm which indicated the site of insertion in the 3' untranslated region of a putative glycosyl transferase gene At1g73160 (FIG. 3).

EXAMPLE 6

Analysis of Expression of the At1g73160 by RT-PCR

To determine if the At1g73160 gene (encoding a putative glycosyl transferase) is expressed in a root-preferential manner, we used gene specific primers primers GLTF (5'-AATGCACCCGAAAGTCTATTTGC-3') (SEQ ID NO:9) and GLTR (5'-AAAACCCTAGGCCCATCTCTTAC-3') (SEQ ID NO:10) to amplify a 345 bp region of the glycosyl tranferase gene. The gene is predicted to lack any intron. Total RNA was isolated from roots and leaves of Columbia plants using Trizol (Gibco-BRL, Life Sciences) according to the manufacturers' protocol. Total RNA was treated with RQ1 RNAse-free Dnase (Promega Inc. Madison, USA) followed by heat inactivation of the enzyme at 80° C.

cDNA synthesis was carried out using the primer GLTR (SEQ ID NO:9) from the gene At1g73160 and GAPC2 (5'-CCTGTTGTCGCCAACGAAGTCAG-3') (SEQ ID NO:11) from the glyceraldehyde phosphate dehydrogenase C gene using 1 µg total DNAse treated RNA in a 20 µl reaction using the Superscript choice system for cDNA synthesis (Gibco-BRL) according to the manufacturers instructions. For PCR amplification, gene-specific primers GLTF (SEQ ID NO:9) and GLTR (SEQ ID NO:10) were used for At1g73160. As a control, GAPC expression was detected using the primers GAPC1 (5'-CTTGAAGGGTGGTGCCAAGAAGG-3') (SEQ ID NO:12) and GAPC2 (SEQ ID NO:11).

Root and leaf samples were isolated from plants grown as described on MS medium. For PCR amplification, 1 µl of 1.5× diluted RT mix was used. The PCR program was as follows; 2 min at 94° C., 35 cycles of 15 sec. at 94° C., 20 sec. at the optimal annealing temperature (55° C.), and 30 sec. at 72° C. A 345 bp amplicon was seen in root RT sample while it was absent in leaf sample. As a negative control, an equivalent amount of root RNA that was directly used for PCR amplification without cDNA synthesis failed to give the amplicon. The specificity of the amplicon was further confirmed by probing a blot containing the RT-PCR samples of root and leaf with $\alpha$-$^{32}$P DATP labeled probe of the 345 bp sequence of the putative glycosyl transferase At1g73160 gene amplified with primers GLTF and GLTR. This observation suggested that the gene expresses tissue preferentially in roots and hence the corresponding promoter could be root preferred (FIG. 4).

EXAMPLE 7

Isolation and Cloning of the At1g73160 Promoter Sequence

Based on the map location of DsE insertion in ETC60, to clone the promoter region of the At1g73160 gene, upstream sequence corresponding to the 572 bp (PGLT1) including 45 bp sequence from the coding region to facilitate GUS translational fusion was amplified using a primer set; ETC60U1 and ETC60D1S. Primer sequences are as follows:

ETC60U1:
(SEQ ID NO:13)
5'-TACCAAGCTTGACAATTTCTCTGAACGGAA-3'

ETC60D1S:
(SEQ ID NO:14)
5'-TGAAGTCGACGGTAATGATTGTTGTGAATCTGAATG-3'

Amplified sequence was cloned in the pMOS vector using pMOS blue blunt end cloning kit (Amersham) according to the manufacturers' instructions. Recombinant plasmid was isolated using plasmid miniprep kit (Qiagen, Germany) according to the manufacturers' instructions. The purified DNA was then sequenced with M13F primer (SEQ ID NO:7) using an automated DNA sequencer ABI 3700 (ABI, Foster City, USA).

EXAMPLE 8

Construction of Binary Vector Containing the GUS Reporter Gene Operably Linked to the At1g73160 Promoter Sequence for Transformation in to Plants The pGLT1, clone described in Example 7 was digested with restriction enzymes Sal1 and Hind III and cloned directionally into a 12 kb Kan$^R$ binary expression vector pBI101.1, resulting in fusion of the regulatory sequence and the N-terminal portion of the gene in frame with the GUS reporter gene in the vector. Kan$^R$ colonies were screened for positives by colony PCR using insert specific primers. Cloning of the insert was also verified by restriction digestion with Sal1 and Hind III enzymes. Recombinant binary vector was then mobilized into an *Agrobacterium* strain AGL1 by tri-parental mating using the *E. coli* strain HB101 harbouring a helper plasmid pRK2013.

EXAMPLE 9

Generation of Transgenic *Arabidopsis* Plants Stably Transformed with the pAt1g73160::GUS Fusion Transformation of *Arabidopsis* Columbia (WT) ecotype:

The promoter-GUS reporter construct was mobilized into *Agrobacterium* strain AGL1, by tri-parental mating. Exconjugants were confirmed for the presence of construct by colony PCR using insert specific primers. The strain AGL1 (pBI101.1::U1) containing the clone carrying 572 bp upstream region including 45 bp coding sequence of At1g73160 gene fused in frame to GUS was used to transform *Arabidopsis* plants by vacuum infiltration [Guang-Ning Ye et al, (1999) The Plant journal, 19(3): 249] Columbia ecotype seeds were sown in light-weight plastic pots containing peat, perlite and vermiculite in 1:1:1 ratio soaked in nutrient solution (½x MS salts), covered with a window mesh and secured with a rubber band. Plants were grown under 16 h light/8 h dark regime and at a temperature of 20° C.

When plants flowered, 500 ml culture of AGL1 (pBI101:: U1) in TYM medium (Bacto-tryptone 5 g; Yeast-extract 0.5 g; Mannitol 10 g; and 1 mM CaCl$_2$.2H$_2$O per litre) containing 50 µg/ml Kanamycin and 50 µg/ml Carbenicillin was grown by inoculating with 1 ml of starter culture at 28° C. Culture was centrifuged at 8000 rpm for 5 minutes and pellet was re-suspended in 250 ml of infiltration medium consisting of 1x MS medium, 50 g sucrose, 0.044 µM benzylaminopurine and 200 µl Silwet L-77 per litre.

Plants containing primary inflorescences of 10–15 cm height with secondary inflorescences appearing at the rosette were used for infiltration. Pots containing plants were inverted into the solution so that the entire plant was covered, including rosette. Pots inverted on infiltration medium were kept in a desiccator and vacuum of 650–700 mm Hg was drawn. Suction was closed and the plants were allowed to stay under vacuum for 10 minutes. Vacuum was released quickly. Pots were placed on their sides in a tray covered with plastic wrap to maintain humidity and were kept in a growth chamber. The next day, pots were set upright and grown under same conditions as before.

Seeds of the transformed plants were collected and screened for Kan$^R$ seedlings. They were assayed for root preferred GUS expression pattern at 4-leaf stage.

EXAMPLE 10

Analysis of GUS Expression in *Arabidopsis* Plants Transformed with the pAt1g73160::GUS Fusion Construct Seeds were harvested from plants used for transformation and screened on MS plates containing 2% sucrose and supplemented with 50 µg/ml Kanamycin for selection of Kan$^R$ transformants. Plants were grown under conditions as described before. Transformant plants were identified based on their green colour and elongated roots. At 4-leaf seedling stage one leaf and a part of the root were stained for each of the T1 Kan$^R$ transgenic plants. In the next generation Kan$^R$ T2 whole plants at 4-leaf seedling stage were screened for root preferred GUS expression pattern by GUS staining as described in Example 2.

The invention claimed is:

1. An expression cassette comprising an isolated promoter sequence comprising the nucleotide sequence set forth in SEQ ID NO:1 or the complement thereof, operably linked to a nucleotide sequence of interest wherein the promoter sequence directs root-preferred expression of the operably linked nucleotide sequence of interest.

2. A method of introducing root-preferred gene expression in a plant said method comprising integrating a nucleic acid comprising the expression cassette according to claim 1 into the genome of the plant, wherein the nucleotide sequence of interest is preferentially expressed in the root of the plant.

3. The method as claimed in claim 2, wherein the method provides improved resistance to soil borne pathogens.

4. A plant cell comprising the expression cassette of claim 1, or a plant comprising the plant cell.

5. The plant cell according to claim4 4, wherein the expression cassette is stably integrated into the genome of the plant cell, or a plant comprising such a plant cell.

6. The plant cell or plant according to claim 4, wherein the plant cell is from, or the plant is, *Arabidopsis*.

7. The plant cell or plant according to claim 4, wherein the plant cell is from, or the plant is, *Brassica*, rice, cotton, mango, wheat, corn, oats, barley, tobacco, ginger, potato, sugarcane, sugar beet, carrot, tomato or soybean.

8. A seed from the plant of claim 5, wherein the expression cassette is stably integrated into the genome of the seed.

9. A vector comprising the expression cassette according to claim 1.

* * * * *

UNITED STATES PATENT AND TRADEMARK OFFICE
CERTIFICATE OF CORRECTION

| | | |
|---|---|---|
| PATENT NO. | : 7,173,166 B2 | Page 1 of 1 |
| APPLICATION NO. | : 10/847539 | |
| DATED | : February 6, 2007 | |
| INVENTOR(S) | : Virupapuram Vijaybhaskar and Imran Siddiqi | |

It is certified that error appears in the above-identified patent and that said Letters Patent is hereby corrected as shown below:

Column 24, Claim 5 line 1

The plant cell according to "claim4" Insert --claim-- 4, wherein the expression cassette is stably integrated into the genome of the plant cell, or a plant comprising such a plant cell.

Signed and Sealed this

Twenty-second Day of May, 2007

JON W. DUDAS
*Director of the United States Patent and Trademark Office*

SEQUENCE LISTING

<160> NUMBER OF SEQ ID NOS: 14

<210> SEQ ID NO 1
<211> LENGTH: 572
<212> TYPE: DNA
<213> ORGANISM: Arabidopsis thaliana

<400> SEQUENCE: 1

```
agaagaagaa agagttgttc ttgaagaatg gttcttgaag gccattgttt tggtttatt      60
gattttgtg aattgagtgc aactattgat gttgattctt tgcttaaatt tcggatcttt     120
ctcgagttat tatatcaaag ttcatttctc aatgacattg cacatggctt agctaatttt    180
tatatggttt ttacattcaa ttgaaagtca aatctctctt aaccaactga gatttgtaac    240
taaaccggga tatcacacct aattagtttt cccggtttga tattttgttt tgtacacgta    300
ggcgtgtgat tactccgtca cactttacac atgtgtaatt cccctaattt atcgggtttc    360
tttaggcgcg tgagataatg cgcgtgtgtc tacgctattc ttgcgacgct gtgcttccta    420
gggtttcgtc gttgcaaaca cagtcaatgt tcatgaacca cggatcctaa tctcccgat     480
cttcgattca ttgtttcaga atccccaat tactgtctct gtgcgtaaaa tctctagaga     540
aaccttaaaa ttttccgttc agagaaattg tc                                  572
```

<210> SEQ ID NO 2
<211> LENGTH: 668
<212> TYPE: DNA
<213> ORGANISM: Arabidopsis thaliana

<400> SEQUENCE: 2

```
gatcccaatg ccattctcta tataaattgt cgcaaccatg tgatgaaaaa acacaacaac     60
ccatctatac cattttctca gctaaaatta aactaacacc tttctaaatt gaaaccattg    120
tcacataaca catggctaac ttgaaattct tgctgtgctt gttcttgatc tgcgtttcct    180
tatcgcgttc atcagcgtct cgaccgatgt tcccaaacgc agacgggatt aaacgagggc    240
gtatgatgat agaagcagag gaagtgttga aagcgagtat ggagaagcta atggagagag    300
gttttaatga gtccatgaga ctcagtcctg gaggtcccga tcctcgccat cactaagtct    360
tattctcgta gttttgaatt cgaggatgta tattttgttc ttgatcgaga accggtttag    420
aagaaaacat atcgatcctc tttgtttgtt tttttttgcct tgtttgttcg ttcggtgtaa    480
ccaatatatt gatgtatctg tttcgttaca catttatgat ttgtgcatgc tttacgtacc    540
ttatacattc cactatatag tagtctagta gagaggagga ctttgcatat aaattgttat    600
ataacaagaa agggtaaaga aatatagtat gataagggag gattgaatta atttaattta    660
tcctgttt                                                              668
```

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: a, c, g, t, unknown, or other
<220> FEATURE:
<221> NAME/KEY: modified_base
<222> LOCATION: (11)

-continued

<223> OTHER INFORMATION: a, c, g, t, unknown, or other

<400> SEQUENCE: 3
ngtcgaswga nawgaa                                              16

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgtttaccg ttttgtatat cccg                                     24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgttccgttt tcgtttttta cc                                       22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtcggtacg gaattctccc                                          20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgccagggtt ttcccagtca cgac                                     24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcggataac aatttcacac agga                                     24

<210> SEQ ID NO 9
<211> LENGTH: 23
<212> TYPE: DNA
<213> ORGANISM: Artificial Sequence

```
-continued

<220> FEATURE:
<223> OTHER INFORMATION: Description of Artificial Sequence: Synthetic
      primer

<400> SEQUENCE: 9
aatgcacccg aaagtctatt tgc                                              23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaccctag gcccatctct tac                                              23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgttgtcg ccaacgaagt cag                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cttgaagggt ggtgccaaga agg                                              23

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taccaagctt gacaatttct ctgaacggaa                                       30

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgaagtcgac ggtaatgatt gttgtgaatc tgaatg                                36
```